United States Patent [19]
Morasse

[11] Patent Number: 6,126,314
[45] Date of Patent: Oct. 3, 2000

[54] MOBILE RADIOGRAPHY DEVICE WITH CASSETTE CONTAINER

[75] Inventor: Louis Morasse, Gif-sur-Yvettes, France

[73] Assignee: GE Medical Systems S.A., France

[21] Appl. No.: 09/214,820

[22] Filed: Jan. 11, 1999

Related U.S. Application Data

[63] Continuation of application No. PCT/FR97/01233, Jul. 8, 1997.

[30] Foreign Application Priority Data

Jul. 9, 1996 [FR] France ................................. 9608543

[51] Int. Cl.⁷ ...................................................... G03B 42/04
[52] U.S. Cl. .............................................................. 378/167
[58] Field of Search ................................. 378/167, 174, 378/197, 198

[56] References Cited

U.S. PATENT DOCUMENTS

| | | | |
|---|---|---|---|
| 4,223,230 | 9/1980 | Waerve et al. | 378/198 |
| 4,387,468 | 6/1983 | Fenne et al. | 378/198 |
| 4,752,948 | 6/1988 | MacMahon | 378/198 |
| 4,885,761 | 12/1989 | Sones et al. | 378/197 |
| 4,955,046 | 9/1990 | Siczek et al. | 378/197 |
| 5,835,558 | 11/1998 | Maschke | 378/198 |

FOREIGN PATENT DOCUMENTS

| | | |
|---|---|---|
| 0000691 | 2/1979 | European Pat. Off. . |
| 872730 | 4/1953 | Germany . |
| 3138916 | 4/1983 | Germany . |

*Primary Examiner*—David V. Bruce
*Assistant Examiner*—Allen C. Ho
*Attorney, Agent, or Firm*—Jay L. Chaskin

[57] ABSTRACT

Mobile radiography device of the type comprising a chassis with wheels, an X-ray generator and a container for a plurality of cassettes each containing a film which is sensitive to X-rays and intended to be developed in a processing room. The cassette container can be separated from the mobile radiography device for the transport of the cassettes to the processing room, the container comprising rolling means and means for gripping by an operator.

20 Claims, 4 Drawing Sheets

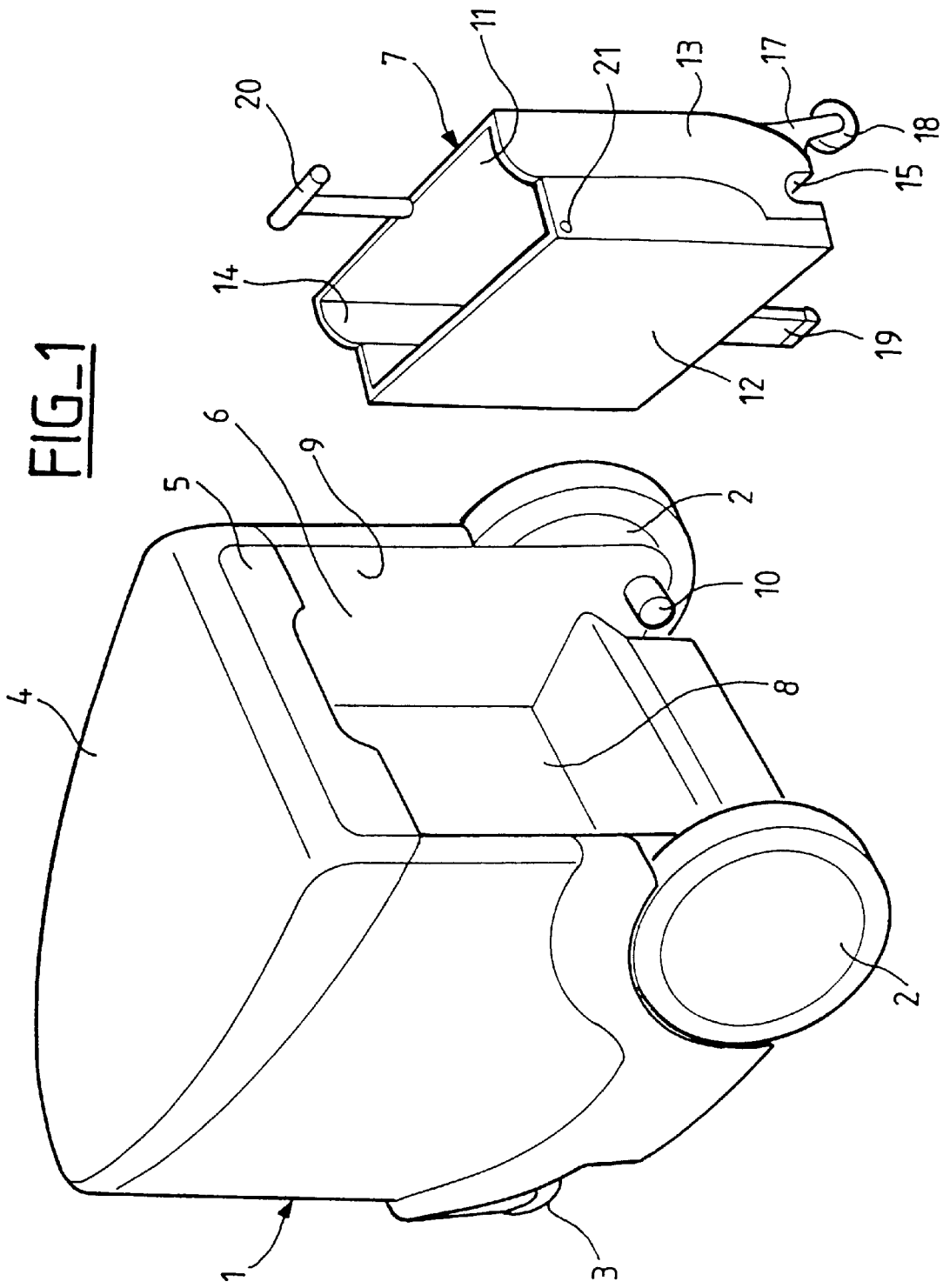
FIG_1

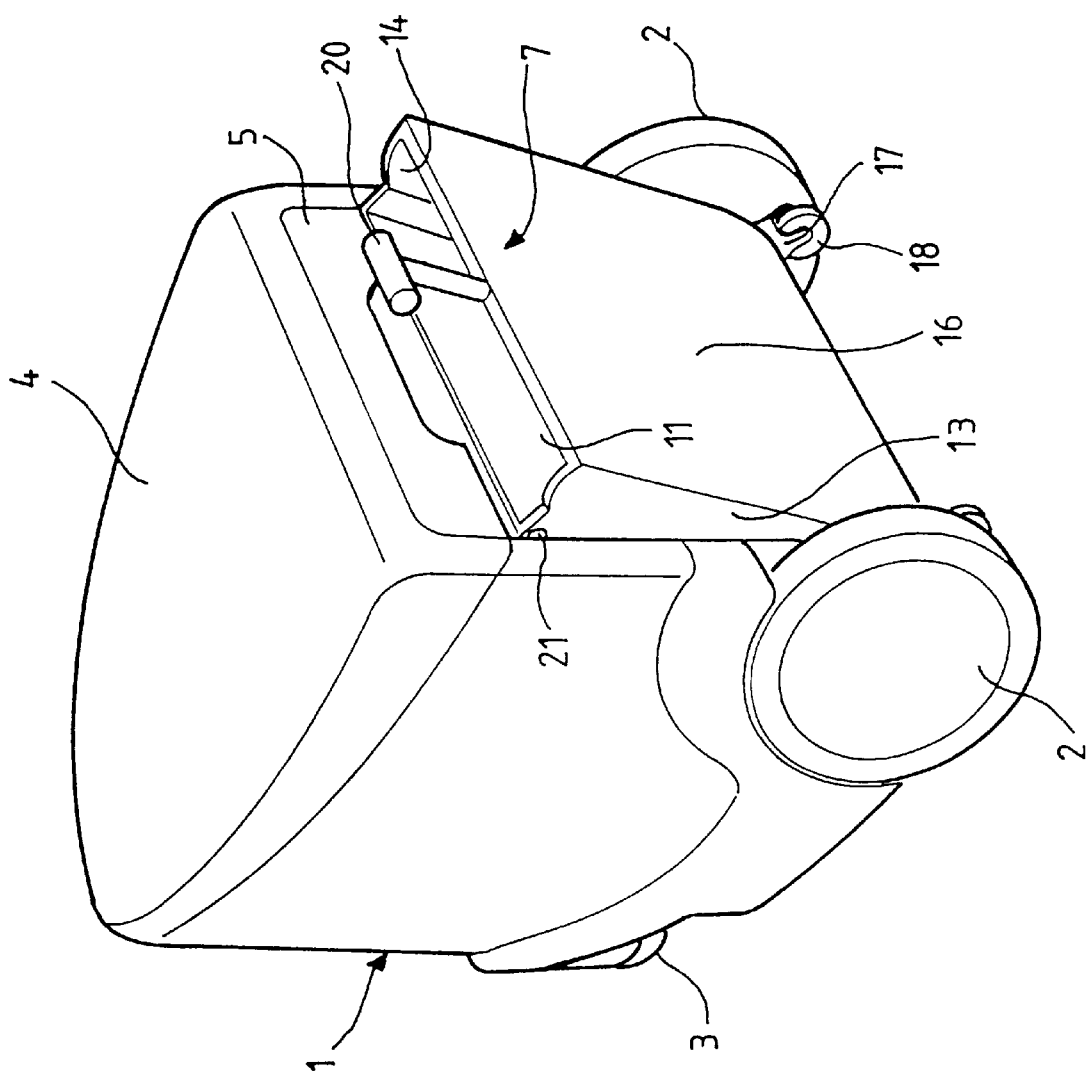
FIG_2

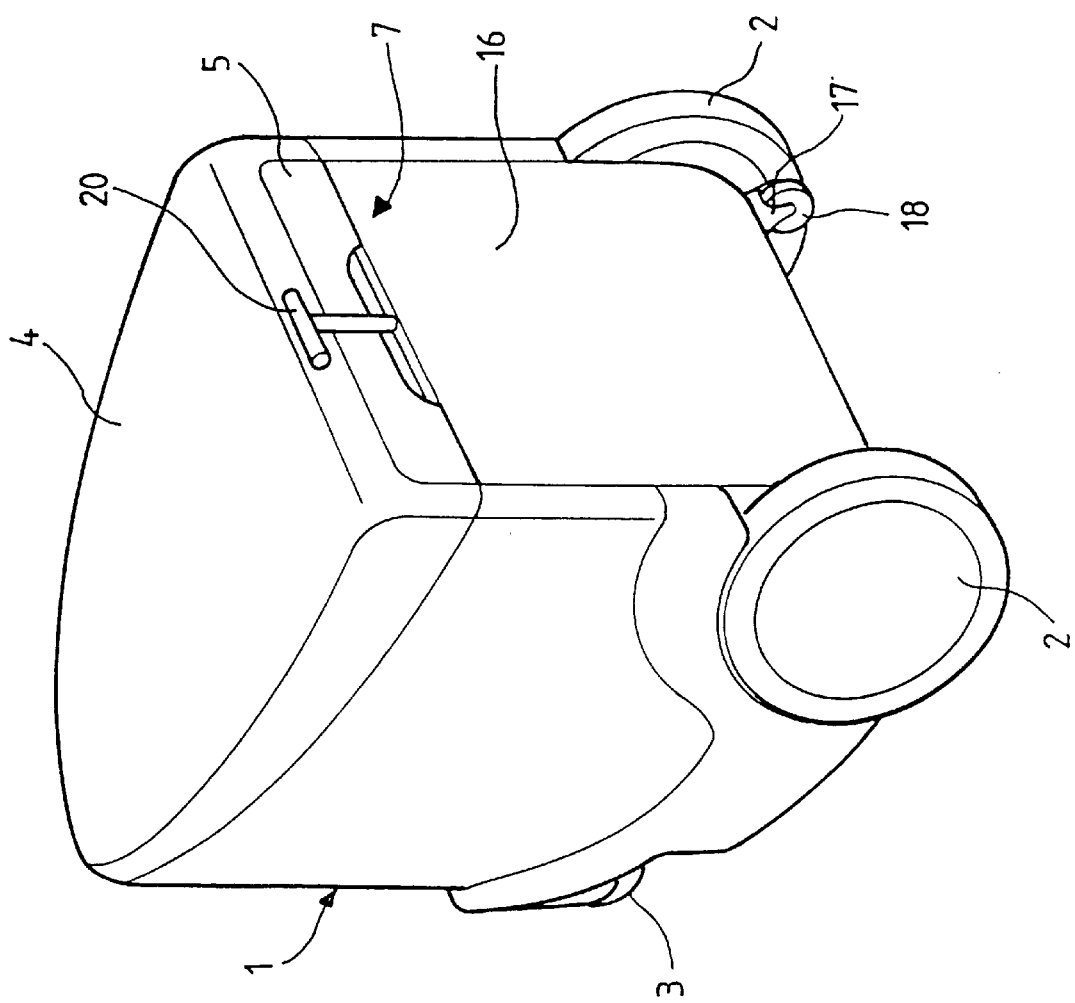

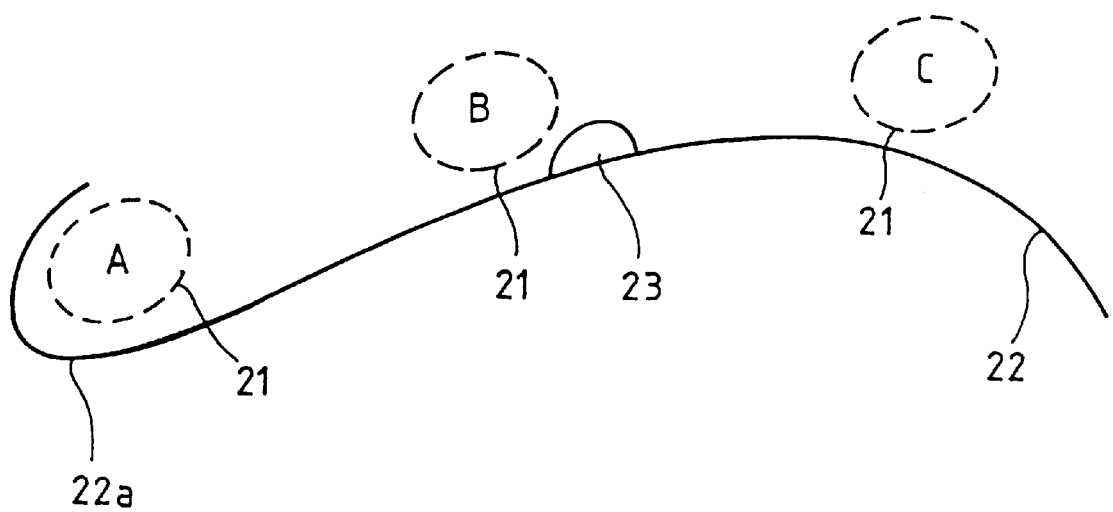
FIG_4

MOBILE RADIOGRAPHY DEVICE WITH CASSETTE CONTAINER

This is a continuation application of International Application No. PCT/FR97/01233 filed Jul. 8 1997.

BACKGROUND OF THE INVENTION

The present invention relates to a mobile radiography device of the type used in hospitals for taking radiographic pictures of various parts of the body of a patient, in the room of the latter, in order to avoid moving the patient.

Therefore, the mobile radiography device is brought close to the bed of the patient and it is arranged so as to take photographs of the part of the body of the patient which is to be subjected to diagnosis.

Mobile radiography devices generally comprise a chassis with wheels, an X-ray generator and a box for a number of cassettes. These cassettes each contain a film which is sensitive to X-rays. The mobile radiography device therefore performs a circuit in the rooms of the different patients, in the course of which the cassettes are used one by one. A blank cassette is taken from the box before the photograph is taken, then the cassette with the exposed film is put back in the box after the photograph has been taken. The cassettes with the exposed film are than transported manually by an operator to a processing room generally situated in the hospital.

However, the cassettes weigh in the region of 900 g each and the operator entrusted with their transport to the processing room frequently has to carry about ten of them. Such a weight is heavy to transport and, since the cassettes have a flat parallelpipedal shape, it is difficult to hold about ten of them at the same time without risking dropping them. Any dropping would risk damaging the cassettes which are relatively expensive and having to take the photographs again.

The aim of the present invention is therefore to overcome the above mentioned disadvantages.

The aim of the present invention is to propose a mobile radiography device, in which any damage to the cassettes by dropping is avoided and in which the laboriousness of the work of the operators is reduced.

The mobile radiography device according to the invention is of the type comprising a chassis with wheels, an X-ray generator and a container for a plurality of cassettes each containing a film which is sensitive to X-rays and intended to be developed in a processing room.

The cassette container can be separated from the mobile radiography device for the transport of said cassettes to the processing room, the container comprising rolling means and means of gripping by an operator.

The operator can thus take a batch of cassettes into the processing room without having to carry them.

BRIEF SUMMARY OF THE INVENTION

In an embodiment of the invention, the mobile radiography device comprises, on a vertical surface, a housing capable of receiving the container, said housing being provided with means for holding the container in a closed position, with means for holding the container in an open position and with means for pivoting the container between said closed and open positions and allowing the separation of the container from the mobile radiography device.

Advantageously, the container comprises a pair of rollers or support elements which are in contact with the ground when the container is separated from the mobile radiography device and raised in relation to the ground when the container is inserted into the housing. The container can comprise a stand for contact with the ground which forms a triangle with the rollers or the support elements for the stability of the container, said container being separated from the mobile radiography device.

Advantageously, the container can comprise means of self-raising in relation to the ground at the time of insertion into the housing. An increase in the rolling resistance of the mobile radiography device is thus avoided.

In an embodiment of the invention, the mobile radiography device comprises a spindle formed by two fingers which project opposite one another in a lower portion of the housing and are capable of interacting with corresponding recesses of the container for the pivoting of said container about said fingers.

In an embodiment of the invention, the mobile radiography device comprises elastic means of holding the container in closed position, arranged in an upper part of the housing.

In a preferred embodiment of the invention, the housing comprises at least one ramp which interacts with at least one protuberance of the container, the protuberance of the container being arranged at one end of the ramp when said container is in closed position, said protuberance being in contact with a holding boss arranged on the ramp when the container is in open position and said protuberance being capable of passing over the holding boss for the purpose of the separation of the container and the mobile radiography device.

In an embodiment of the invention, the container comprises a transport handle. This handle can be retractable in order to be inserted into the housing and avoid forming a bump interfering with the use of the mobile radiography device.

Thanks to the invention, a cassette container is obtained, which is removable in relation to the radiography device and which can be arranged in a closed position, in an open position, for example to take out or put back in a cassette, and in a position in which it is separated from the mobile radiography device for the transport of the cassettes to a processing room.

BRIEF DESCRIPTION OF THE DRAWINGS

The invention will be better understood by studying the detailed description of an embodiment taken by way of a non-limiting example and illustrated by the attached drawings, in which:

FIG. 1 is a perspective view of the mobile radiography device and of the removable container separated from one another;

FIG. 2 is a perspective view of the mobile radiography device equipped with the container in the open position;

FIG. 3 is a view similar to FIG. 2 with the container in the closed position, and FIG. 4 is a diagrammatic view of the profile of the ramp.

DETAILED DESCRIPTION OF THE INVENTION

As can be seen in the figures, the mobile radiography apparatus comprises a chassis 1 resting on the ground by means of a pair of rear fixed-axle wheels 2 and one pivoting front wheel 3. The chassis 1 comprises an upper face 4 and a rear face 5. On the upper face 4, a keyboard (not shown)

for controlling the radiography operations, and an articulated arm (not shown) supporting the X-ray generator and intended to come close to the body of the patient, can be provided. The rear face 5 is hollow so as to define a housing 6 intended to receive the mobile container 7. The housing 6 of essentially parallelepipedal shape comprises an end wall 8 and two lateral walls 9, only one of which is visible in FIG. 1. The lower end of each lateral wall 9 of the housing 6 is provided with a cylindrical finger 10, of a diameter which corresponds essentially to its length, which is perpendicular to the wall 9 and projects towards the inside of the housing 6. The two fingers 10 are coaxial and form a pivoting spindle.

The container 7, whose shape conforms with that of the housing 6, comprises a hollow upper face 11 intended to receive the cassettes used in mobile radiography apparatuses and generally containing a film sensitive to X-rays, the exposed film then being subjected to a developing operation.

The container 7 also comprises a rear face 12 and two lateral f aces 13 and 14. The lateral face 13 comprises at its lower end a recess 15 capable of interacting with a finger 10 of the housing 6. The lateral face 14 also comprises a recess identical to the recess 15. The container 7 comprises a front face 16, close to the lower end of which two feet 17 are arranged, which each support a roller 18. The feet 17 extend lower than the lower end of the front face 16 so as to be in contact with the ground when the container 7 is separated from the mobile radiography device (FIG. 1).

Opposite, on the side of the rear face 12, the container 7 comprises a stand 19 which is capable of coming into contact with the ground to form with the rollers 18 a triangle of support. The container 7 also comprises a handle 20 which projects upwards from the upper face 14. The handle 20 is fixed but a retractable handle could be provided in order to avoid it being caught accidentally by an operator.

When a photograph is being taken, the radiography apparatus is in the position illustrated in FIG. 3 with the container 7 in place in its housing 6 and closed. The rollers 18 and the stand 19 are then raised in relation to the ground in order to avoid unnecessarily increasing the resistance to advance of the radiography apparatus.

After the photograph has been taken, the operator opens the container 7 by means of the handle 20 by making its upper end pivot towards the rear, the lower end pivoting about the pivoting fingers 10 by means of the recesses 15. The operator can then place the cassette with the exposed film in the container 7. To facilitate differentiation between cassettes which are already used and blank cassettes, the compartment defined by the hollow face 11 of the container 7 can be divided into two parts, one for the cassettes which have already been used and the other for the blank cassettes. The radiography apparatus is then in the position illustrated in FIG. 2. Lastly, the operator can continue to pull the handle 20 of the container 7, which causes the complete separation of the radiography apparatus and the container 7 as illustrated in FIG. 1.

The lateral face 13 of the container 7 is provided with a protuberance 21 which is capable of interacting with a ramp provided on the inside of the housing 6, the profile of which is shown in FIG. 4. The ramp 22 is of rounded shape to interact with the trajectory of the protuberance 21 of the lateral face 13 of the container 7. When the protuberance 21 is in position A, that is to say in the bottom 22a of the ramp 22, the container 7 is in the closed position illustrated in FIG. 3. Then, when the container 7 is arranged in the open position, the protuberance 21 is in position B close to the boss 23. The boss 23, arranged on the ramp 22, serves as a stop for the protuberance 21 to hold the container 7 in open position, illustrated in FIG. 2, without complete separation of the container 7 and the radiography apparatus.

When the operator desires a complete separation, he is then obliged to raise the container 7 slightly so that the protuberance 21 passes over the boss 23. As can be seen in FIG. 1, this slight raising is compatible with the interaction of the recesses 15 with the pivoting fingers 10. After the boss 23 has been passed over, the protuberance 21 is in position C. and leaves the ramp 22, the container 7 then separating from the radiography apparatus.

The insertion of the container 7 into the radiography apparatus is carried out in reverse. The operator holds the container 7 by the handle 20 and presents it facing the housing 6. He can then incline the container 7 a little more so as to facilitate its insertion into the housing 6 and to bring about a lever effect about the pivoting fingers 10 in order to avoid having to carry the container 7 during its raising, the rollers 18 being raised in relation to the ground. The operator then has the choice between leaving the container in open position or reclosing it completely. To hold the container 7 in closed position, it is possible to provide holding means such as elastic tongues arranged in the top of the housing 6 to avoid untimely opening of the container 7.

Thanks to the invention, a mobile radiography device is obtained, which is equipped with a removable container which makes the transport of the cassettes to the processing room less laborious, which reduces the risk of damage to the cassettes by dropping and which is easy to insert into and extract from the housing of the radiography apparatus.

Various modifications in structure and/or function and/or steps may be made by one skilled in the art without departing from the scope and extent of the invention.

What is claimed is:

1. Mobile radiography device comprising a chassis with wheels, a generator of radiation and a container for a plurality of cassettes each containing a film which is sensitive to the radiation wherein the cassette container can be separated from the mobile radiography device for the transport of the cassettes to a processing unit, the container comprising rolling means and means for gripping by an operator.

2. Device according to claim 1 comprising, on a vertical surface a housing capable of receiving the container, the housing being provided with means for holding the container in a closed position, with means for holding the container in an open position and with means for pivoting the container between the closed and open positions and allowing the separation of the container from the mobile radiography device.

3. Device according to claim 1 wherein the container comprises support elements which are in contact with the ground when the container is separated from the mobile radiography device and raised in relation to the ground when the container is inserted into the housing.

4. Device according to claim 3 wherein the container comprises a stand for contact with the ground which forms a triangle with the support elements for the stability of the container, the container being separated from the mobile radiography device.

5. Device according to claim 3 wherein the container comprises means for self-raising in relation to the ground at the time of insertion into the housing.

6. Device according to claim 4 wherein the container comprises means for self-raising in relation to the ground at the time of insertion into the housing.

7. Device according to claim 2 comprising a spindle formed by two fingers which project opposite one another in a lower portion of the housing and are capable of interacting with corresponding recesses of the container for the pivoting of the container about the fingers.

8. Device according to claim 3 comprising a spindle formed by two fingers which project opposite one another in a lower portion of the housing and are capable of interacting with corresponding recesses of the container for the pivoting of the container about the fingers.

9. Device according to claim 4 comprising a spindle formed by two fingers which project opposite one another in a lower portion of the housing and are capable of interacting with corresponding recesses of the container for the pivoting of the container about the fingers.

10. Device according to claim 5 comprising a spindle formed by two fingers which project opposite one another in a lower portion of the housing and are capable of interacting with corresponding recesses of the container for the pivoting of the container about the fingers.

11. Device according to claim 2 comprising elastic means for holding the container in closed position, arranged in an upper part of the housing.

12. Device according to claim 3 comprising elastic means for holding the container in closed position, arranged in an upper part of the housing.

13. Device according to claim 4 comprising elastic means for holding the container in closed position, arranged in an upper part of the housing.

14. Device according to claim 5 comprising elastic means for holding the container in closed position, arranged in an upper part of the housing.

15. Device according to claim 6 comprising elastic means for holding the container in closed position, arranged in an upper part of the housing.

16. Device according to claim 7 comprising elastic means for holding the container in closed position, arranged in an upper part of the housing.

17. Device according to claim 2 wherein the housing comprises at least one ramp which interacts with at least one protuberance of the container, the protuberance of the container being arranged at one end of the ramp when the container is in closed position, the protuberance being in contact with a holding boss arranged on the ramp when the container is in open position and the protuberance being capable of passing over the holding boss for the purpose of the separation of the container and the mobile radiography device.

18. Device according to claim 3 wherein the housing comprises at least one ramp which interacts with at least one protuberance of the container, the protuberance of the container being arranged at one end of the ramp when the container is in closed position, the protuberance being in contact with a holding boss arranged on the ramp when the container is in open position and the protuberance being capable of passing over the holding boss for the purpose of the separation of the container and the mobile radiography device.

19. Device according to claim 1 wherein the container comprises a transport handle.

20. Device according to claim 19 wherein the handle is retractable in order to be inserted into the housing.

* * * * *